(12) United States Patent
Kim (10) Patent No.: US 7,763,284 B2
(45) Date of Patent: *Jul. 27, 2010

(54) METHOD FOR TREATING OR PREVENTING SYMPTOMS ASSOCIATED WITH MENOPAUSE

(75) Inventor: Jae-Soo Kim, Seoul (KR)

(73) Assignee: Naturalendo Tech Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 11/393,952

(22) Filed: Mar. 31, 2006

(65) Prior Publication Data

US 2006/0193929 A1 Aug. 31, 2006

Related U.S. Application Data

(63) Continuation-in-part of application No. 10/523,645, filed as application No. PCT/KR03/01574 on Aug. 6, 2003, now abandoned.

(51) Int. Cl.
*A01N 65/00* (2009.01)
(52) U.S. Cl. ..................................................... 424/725
(58) Field of Classification Search .................. None
See application file for complete search history.

(56) References Cited

U.S. PATENT DOCUMENTS 5,597,585 A * 1/1997 Williams et al. ............. 424/579
6,413,554 B1 * 7/2002 No .............................. 424/739
7,074,435 B2 * 7/2006 Cho et al. .................... 424/725

FOREIGN PATENT DOCUMENTS

WO WO 02/47702 A1 6/2002

OTHER PUBLICATIONS

Han et al., Journal of Nutrition, 2000, 130:2760-2764.*
Fleisch, Herbert; "Bisphosphonates: Mechanics in Action"; Endocrine Reviews; vol. 19; Feb. 1998; pp. 80-100.
Shaw, N. J., and Bishop, N.J.; "Bisphosphonate Treatment of Bone Disease"; Archives of Disease in Childhood; vol. 90, Issue 5; May 2005; pp. 494-499.
Stearns, Vered, et al.; "Paroxetine Controlled Release in the Treatment of Menopausal Hot Flashes: A Randomized Controlled Trial"; The Journal of the American Medical Association; vol. 289; No. 21; Jun. 4, 2003, pp. 2827-2834.
Wyeth-Ayerst Laboratories; "The New Science of Estrogen Receptors"; U.S. Pharmacist; U.S. Pharmacist Continuing Education, ACPE Program No. 430-000-99-004-H01.
Kwak, Bo-Yeon, "Binding Affinity of EstroG to ER alpha and beta"; Mar. 28, 2008.
Final Office Action dated Jan. 6, 2010 for U.S. Appl. No. 11/834,953.

* cited by examiner

*Primary Examiner*—Michael V Meller
(74) *Attorney, Agent, or Firm*—Ked & Associates, LLP (57) ABSTRACT

The present invention relates to a composition for accelerating secretion of estrogen and regenerating tissue cells of female sexual organs, and a method for treating or preventing a disease, disorder or symptom associated with menopause. The present invention uses a composition comprising as an active ingredient an extract from *Cynanchum wilfordii*, an extract from *Phlomis umbrosa* or its combination. The composition may further comprise as an active ingredient an extract from an extract from *Platycodon grandiflorum* and/or an extract from *Angelica gigas*.

6 Claims, 6 Drawing Sheets

METHOD FOR TREATING OR PREVENTING SYMPTOMS ASSOCIATED WITH MENOPAUSE

CROSS-REFERENCE TO RELATED APPLICATIONS

This is a continuation-in-part of U.S. application Ser. No. 10/523,645, filed Feb. 4, 2005 now abandoned, which is a 371 of PCT/KR2003/001574, filed Aug. 6, 2003.

BACKGROUND OF THE INVENTION

1. Field of the Invention

The present invention relates to a composition for accelerating secretion of estrogen and regenerating tissue cells of female sexual organs and a method for treating or preventing a disease, disorder or symptom associated with menopause.

2. Description of the Related Art

A hormone secreted from follicles in ovaries, estrogen, develops sexual organs and makes them functional to exhibit the secondary sexual character and accelerate the development of uterus, the growth of endometrium, the development of mammary gland and regular menstruation. In addition to ovaries, estrogen is secreted from placenta, adrenal cortex and testis in a small amount. Three types of steroids, estrone, estradiol and estriol found in body are known.

Estrogen is produced from androgenic precursors through an enzymatic process, aromatization. 17 beta-estradiol (E2), a strong estrogen, which exists predominantly in premenopausal women is synthesized during the formation of follicle, is secreted to blood stream and bound to sex hormone binding globulin in a portion, and then circulates to cells in body. The main metabolic pathway of estradiol is to be oxidized reversibly to estrone, a weak estrogen and finally converted to estriol (E3). Estrone is produced by aromatization of androstenedione, precursor of androgen, in the peripheral tissue. The above compounds are metabolized to form sulfate and glucuronide and excreted (Lievertz R W. Pharmacology and pharmacokinetics of estrogen. *Am J Obstet Gynecol* 156: 1289-1293(1987)). As aromatization occurs in adipose tissue, those who have many adipose tissues have more estrogen. Estradiol and estrone may be metabolized in liver to estriol, very weak estrogen (Anderson F. Kinetics and pharmacology of estrogens in pre- and postmenopausal women. *Int J Fertil* 38 (suppl 1):53-64 (1993)). Other estrogen metabolites as well as estradiol and estrone could function like estrogen. Therefore, it could be understood that the systematic estrogen effects in women depends on both estrogen and its metabolites.

The average concentrations of estradiol and estrone are 520 pg/ml and 3,070 pg/ml respectively. The peak concentrations of estradiol and estrone are 200-400 pg/ml and 170-200 pg/ml respectively in ovulation phase and decrease to the minimum concentrations of 40-60 pg/ml and 40-60 pg/ml respectively in the early stage of menstruation.

The ratio of estradiol to estrone in premenopause is generally lager than 1 (Odonnell M B. Pharmacokinetic and pharmacologic variation between different estrogen products. *J Clin Pharmacol* 35 (suppl):18S-24S (1995)). In postmenopause, estrone produced by conversion of adrenal androstenedione becomes a major estrogen.

The metabolic pathway including 2-hydroxyation is more complicated and results in the formation of catecholesterogen. This pathway is more important in the central nervous system such as brain than in the peripheral tissue. Estrogen exhibits its effects by modification of catecholamine metabolite (Lievertz R W. Pharmacology and pharmacokinetics of estrogen. Am J Obstet Gynecol 156:1289-1293(1987)). Since catecholamine interacts with dophamin (a precursor of adrenalin) receptor, alpha 1-adrenalin receptor and serotonin receptor, it is considered to be important. Furthermore, the hydroxy derivatives of estrogen play other roles. For example, 4-hydroxy estrogen functions like estrogen; however, 2-hydoxy estrogen does not. However, 2-hydroxy derivatives of estradiol functions not only like estrogen, but also catecholamine (Lievertz R W. Pharmacology and pharmacokinetics of estrogen. *Am J Obstet Gynecol* 156:1289-1293(1987)). This accounts partially for the mechanism how estrogen has an effect on the central nervous system.

The main physiological functions of estrogn is to regulate the development, differentiation and action of sexual tissues including mammary gland, uterus and ovaries (Kuiper G G J M, Carlsson B, Grandien K, et al. Comparison of the ligand binding specificity and transcript tissue distribution of estrogen receptors alpha and beta. *Endocrinology* 138:863-870 (1997)). Estrogne stimulates the growth of endometrium, myometrium, vagina and urethral epithelium. Estrogen also functions in the smooth flow of blood in sexual tissues, the increase of secretion in uterine gland and induces the expression of progesterone and luteinzing hormone receptor. Estrogen has an effect on the growth and development of backbone, fat distribution in women and lipid metabolite as well as female sexual organs and the secondary sexual character. Estrogen plays roles in skin, collagen tissue, neuron and cardiovascular system.

Estrogen deficiency brings up the symptoms such as hot flashes caused from vasomotor instability and in the long term, urogenital degeneration, osteoporosis, tooth loss, arteriosclerosis and coronary heart disease, etc., occasionally resulting in dementia (Maddox R W, Carson D S, Barnes C L. Estrogens and postmenopausal women. *US Pharmacist* 23:141-150(1998); and Guyton A C, Hall J E. Textbook of Medical Physiology. 9th ed. *Philadelphia*: W. B. Saunders, 1996).

In postmenopause, women experience various menopausal symptoms such as blushing and depression caused from the decreased estrogen secretion in function-deteriorated ovarian. For a hormone replacement therapy, the postmenopausal women lack of estrogen is administered with extrinsic estrogen to reduce the risk of disease occurrence.

Administering estrogen into postmenopausal women improves vasomotion and urogenital diseases, protects and controls osteoporosis and reduces the risk of coronary heart disease (Maddox R W, Carson D S, Barnes C L. Estrogens and postmenopausal women. *US Pharmacist* 23:141-150(1998)).

However, the problem is that such a hormone replacement therapy may increase the activity of cancer-inducing gene, leading to increased incidence rate of breast cancer and metrocarcinoma, etc.

The known estrogen-replacing agents are artificially synthesized or available from natural source. For example, premarin made from horse urine increases the concentration of estradiol and estrone up to that in secretion phase (Stumpf P G. Pharmacokinetics of estrogen. *Obstet Gynecol* 75 (suppl): 9S-14S(1990)). However, as the source of the product is horse urine, the patient compliance is far poor.

As the example of plant products, mexico yam contains steroid precursor used for synthesizing esterified-estrogen (estrogen sodium salt mixture comprised of estrone 75%-85% and equiline 6%-15% as main components) (e.g., estratab, Menest). Such plants as soy bean, date palm and pomegranate contain nonsteroid plant compound, phytoestrogen. Natural estroen originated from these plant functions as agonists and/or antagonist (Barrett J. Phytoestrogens: friends or foes? *Environ Health Perspect* 104:478-482 (1996)).

17 beta-estradiol, estrone, estrogen sulfate are the exmples of chemically modified estrogen. Such synthesized estrogen is used generally as an oral contraceptive, but hardly in hormone replacement therapy.

In short, the amount of estrogen secreted decreases with aging and the pattern of estrogen secretion is directly related to the advancement of aging. It has been recognized in the art that the administration of hormone replacement therapy allows to improve the usual symptoms of menopause, while the conventional hormone replacement therapy gives rise to severe adverse-effects.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive study to overcome the defects of estrogen replacement therapy. As a result, the inventors have found that a novel composition comprising plant extracts from *Platycodon grandiflorum*, *Cynanchum wilfordii*, *Phlomis umbrosa* and/or *Angelica gigas* permits to treat, prevent and ameliorate symptoms associated with menopause.

Accordingly, it is an object of this invention to provide a composition for accelerating estrogen secretion.

It is another object of this invention to provide a method for treating or preventing a disease, disorder or symptoms associated with menopause.

Other objects and advantages of the present invention will become apparent from examples to follow, appended claims and drawings.

DETAILED DESCRIPTION OF THIS INVETNION

In one aspect of this invention, there is provided a composition for accelerating estrogen secretion, which comprises one or more of *Platycodi Radix* and *Cynanchum wilfordii* extracts as active ingredient.

According to the present invention, a natural source, *Platycodi Radix* refers to a root of *Platycodon grandiflorum* belonging to perennial plant, *Campanulaceae*, and contains not only tens types of saponin glycosides such as flaticodion-A, C, D1 and D2, flaticodigenin, but also polygalacine-D1 and D2 in addition to betulin, enutin and phytosterol. It has been known that *Platycodi Radix* exhibits expectoral, antitussive, anti-inflammatory and antipyretic efficacy.

Additionally, a raw material, *Cynanchum wilfordii* is a perennial plant belonging to *Polygonaceae* with height of 1-3 m. Its root is tuberous and thick. It contains cinancotoxin and phytotocotoxin and used as tonics The present inventors have screened out various natural sources to search material capable of increasing estrogen concentration in blood by accelerating estrogen secretion and found that the extracts obtained from *Platycodi Radix* or *Cynanchum wilfordii* have such activity.

According to a preferred embodiment of this invention, the composition of the present invention comprises further the extract obtained from *Phlomis umbrosa*.

*Phlomis umbrosa* used in the present invention is a perennial plant belonging to *Labiatae* with height of 70-150 cm. It has 5 tuberous roots. Its leave is edible and its root and rhizome is used for medicines. *Phlomis umbrosa* extract of the present invention protects ovaries and induces estrogen secretion (see the Korean Unexamined Pat. Publication No. 1998-61480).

Furthermore, the present inventors found that the composition comprising *Platycodi Radix*, *Cynanchum wilfordii* and *Phlomis umbrosa* extracts exhibits synergic effect on accelerating estrogen secretion.

The extracts of *Platycodi Radix*, *Cynanchum wilfordii* and *Phlomis umbrosa* used as active ingredients in the present invention exhibits excellent efficacy in accelerating estrogen secretion without adverse effects such as cancer occurrence, compared with conventional hormone replacement therapy.

The extracts of *Cynanchum wilfordii* and *Phlomis umbrosa* used in the present invention may be provided from various organs and tissues (e.g., stem, leave, root, fruit and seed, etc) of *Cynanchum wilfordii* and *Phlomis umbrosa*, and the most preferable extract is that obtained from root thereof.

The extracts from *Platycodi Radix*, *Cynanchum wilfordii* or *Phlomis umbrosa* are obtained using various extraction solvents: (a) water, (b) absolute or water-bearing lower alcohol containing 1-4 carbon atoms (methanol, ethanol, propanol, butanol, etc.), (c) mixture of lower alcohol and water, (d) acetone, (e) ethyl acetate, (f) chloroform, (g) 1,3-butylene glycol and (h) butyl acetate. Most preferably, the extracts of this invention is obtained using water as extraction solvent. Furthermore, it is apparent to one skilled in the art that other conventional solvents may be employed for substantially identical extraction efficiency.

The extracts of this invention include those subject to additional purification by the well-known methods in the art as well as those obtained by extraction. For instance, it could be appreciated that active fractions obtained using a variety of additional purification methods such as an ultrafiltration with defined molecular weight cut-off value and various chromatography (designed for purification dependent upon size, charge, hydrophobicity and affinity) are included in the present extracts.

Preferably, the extracts of this invention are active fractions obtained by ultrafiltration membrane with low molecular weight cut off range, more preferably by extracting *Platycodi Radix* and *Cynanchum wilfordii* with hot water, whereby a crude extract is obtained; and filtering the crude extract by means of ultrafiltration membrane with molecular weight cut off of 50,000-100,000 and most preferably by means of ultrafiltration membrane with molecular weight cut off of 100,000. The extracts of this invention can be obtained in the form of powder by use of vacuum distillation, lyophilization or spray drying.

The composition of the present invention for accelerating estrogen secretion prevents the degeneration of female sexual organ by the regeneration or propagation of various tissue cells of female sexual organs such as ovarian, uterus, vagina and oviduct.

According to a preferred embodiment of this invention, the amount of *Platycodi Radix, Cynanchum wilfordii* or *Phlomis umbrosa* extracts in the composition of this invention as active ingredients is 20-80% by weight based on the total amount of composition, more preferably 25-30% by weight, and most preferably 27% by weight. According to the composition comprising more than two of the extracts, the amount of the extracts is 20-80% by weight of the total amount of composition.

According to a preferred embodiment of this invention, the composition of the present invention may further comprise one or more of calcium, arginin, lysine and various Vitamins. Calcium plays the secondary role in preventing osteoporosis by strengthening the bones of women in menopause, being necessary for muscle motion and involved in neural transmission, blood coagulation, activation of hormones and enzymes, anti-inflammation and alleviation of insomnia. Arginin, an essential amino acid needed for the synthesis and degradation of growth hormone, is involved in muscle development, removal of lipids, regeneration of cell and immune-boosting. Lysine is helpful in body growth, calcium-absorption and biosynthesis of collagen, antibodies and enzymes. Such additional ingredients could elevate the efficacy of the present plant extracts.

Meanwhile, the composition of the present invention comprising one or more of *Platycodi Radix* and *Cynanchum wilfordii* extract and/or *Phlomis umbrosa* extract shows the efficacy in vivo such as induction of estrogen secretion and regeneration or propagation of tissue cells of female sexual organ.

In another aspect of this invention, there is provided a pharmaceutical composition for treating or preventing a disorder associated with menopause, which comprises a pharmaceutically effective amount of one or more of *Platycodi Radix* and *Cynanchum wilfordii* extracts; and a pharmaceutical acceptable carrier.

In addition, a pharmaceutical composition of the present invention may further comprise Phlomis umbrosa extract as active ingredient.

A pharmaceutical composition of the present invention comprising a pharmaceutically effective amount of one or more of *Platycodi Radix* and *Cynanchum wilfordii* extract and/or *Phlomis umbrosa* extract is useful for treating or preventing a disorder associated with menopause developed after menopause. Such disorders include hot flush due to poor vasomotion, blushing on face, night sweating, climactic diseases, osteoporosis, disease in genitourinary system, cardiovascular diseases, dementia, tooth loss and skin collagen loss.

The pharmaceutical composition of the present invention comprising a pharmaceutically effective amount of one or more of *Platycodi Radix* and *Cynanchum wilfordii* extract and/or *Phlomis umbrosa* extract is advantageous to efficient and radical treatment of disorder associated with menopause, since it can induce estrogen secretion in vivo.

A pharmaceutical composition of the present invention has much less adverse effects, particularly the incidence of cancers such as metrocarcinoma and breast cancer than conventional hormone replacement therapy.

In the pharmaceutical compositions of this invention, the pharmaceutically acceptable carrier may be conventional one for formulation, including carbohydrates (e.g., lactose, amylose, dextrose, sucrose, sorbitol, mannitol, starch, cellulose), gum acacia, calcium phosphate, alginate, gelatin, calcium silicate, microcrystalline cellulose, polyvinylpyrrolidone, water, salt solutions, alcohols, gum arabic, syrup, vegetable oils (e.g., corn oil, cotton-seed oil, peanut oil, olive oil, coconut oil), polyethylene glycols, methyl cellulose, methylhydroxy benzoate, propylhydroxy benzoate, talc, magnesium stearate and mineral oil, but not limited to. The pharmaceutical compositions of this invention, further may contain wetting agent, sweetening agent, emulsifier, buffer, suspending agent, preservatives, flavors, perfumes, lubricant, stabilizer, or mixtures of these substances.

The pharmaceutical composition of this invention may be administered orally or parenterally. For non-oral administration, intravenous injection, subcutaneous injection, intramuscular injection, nasal spray, sublingual spray may be employed. Preferred method is oral administration or sublingual spray and the most preferred is oral administration.

The correct dosage of the pharmaceutical compositions of this invention will be varied according to the particular formulation, the mode of application, age, body weight and sex of the patient, diet, time of administration, condition of the patient, drug combinations, reaction sensitivities and severity of the disease. It is understood that the ordinary skilled physician will readily be able to determine and prescribe a correct dosage of this pharmaceutical compositions. According to a preferred embodiment of this invention, where the pharmaceutical compositions is orally administered, suitable dosage unit for human host is to administer once a day with the composition containing 0.1-5 g of *Platycodi Radix, Cynanchum wilfordii*, or *Phlomis umbrosa* extract, the most preferred with the composition containing 2 g of the extracts.

According to the conventional techniques known to those skilled in the art, the pharmaceutical compositions of this invention can be formulated with pharmaceutical acceptable carrier and/or vehicle as described above, finally providing several forms including a unit dosage form. Non-limiting examples of the formulations include, but not limited to, a solution, a suspension or an emulsion, an extract, an elixir, a powder, a granule, a tablet, a capsule, emplastra, a liniment, a lotion and an ointment.

In further aspect of this invention, there is provided a food composition for accelerating estrogen secretion, which comprises one or more of *Platycodi Radix* and *Cynanchum wilfordii* extracts as active ingredient.

In addition, a food composition of the present invention may further comprise *Phlomis umbrosa* extract as active ingredient.

In the food composition of this invention, it can comprise typical ingredients incorporated into food products known to one skilled in the art. For example, for preparation of dirnks, citric acid, liquid fructose, sucrose, glucose, acetic acid, malic acid, fruit juice, *Eucommiae Cortex* extract, *Zizyphus jujuba* extract and *Glycyrrhiza, Liquorice* extract may be further included in addition to *Platycodi Radix, Cynanchum wilfordii* or *Phlomis umbrosa* extract. A food of the present invention is very effective in treating or preventing a disorder associated with meonpasue caused by reduced estrogen secretion level.

The composition of the present invention not only induces estrogen secretion and regenerates or propagates tissue cells of sexual organs, but also has much less adverse effects than those chemically synthesized since it comprises *Platycodi*

Radix and *Cynanchum wilfordii* extracts and/or *Phlomis umbrosa* extract used traditionally as oriental pharmaceuticals.

In still another aspect of this invention, there is provided a method for treating or preventing a disease, disorder or symptom associated with menopause, which comprises administering to a subject an effective amount of a composition comprising as an active ingredient an extract from *Cynanchum wilfordii*, an extract from *Phlomis umbrosa* or its combination.

As clearly demonstrated in Examples, in particular, the clinical test, the present composition of this invention exhibits significant efficacy in treating, preventing or ameliorating a disease, disorder or symptom associated with menopause.

According to a preferred embodiment, the composition further comprises as the active ingredient an extract from *Platycodon grandiflorum*. Also, it is preferred that the composition further comprises as the active ingredient an extract from an extract from *Angelica gigas*.

According to more preferred embodiment, the composition of this invention comprises three types of plant extracts from *Platycodon grandiflorum, Cynanchum wilfordii* and *Phlomis umbrosa*.

Alternatively, it is more preferred that the composition of this invention comprises three types of plant extracts from *Cynanchum wilfordii, Phlomis umbrosa* and *Angelica gigas*.

The present composition may be prepared as a pharmaceutical, health supplement or food composition. General descriptions for pharmaceutical, health supplement and food compositions follow those discussed hereinabove. Preferably, the composition of this invention is administered orally. The dosage of the composition of this invention will be varied. Preferably, the daily dose of the composition of this invention comprises 400-1000 mg of the active ingredients.

According to a preferred embodiment, the composition of this invention further comprises one or more ingredients selected from the group consisting of calcium, arginin, lysine and various Vitamins.

According to a preferred embodiment, the plant extract is an active fraction prepared in a process which comprises contacting *Platycodon grandiflorum, Cynanchum wilfordii, Phlomis umbrosa* or *Angelica gigas* with a hot water for obtaining an extract; and filtering the extract through an ultrafiltration membrane with a molecular weight cut off of 50,000-100,000.

The present method is very effective in treating, preventing or ameliorating a disease, disorder or symptom associated with menopause such as climacteric symptoms (e.g., dyspareunia, hot flush, sleep disorder, mental awareness problem, joint pain, musculoskeletal disease, dyspepsia, urinary incontinence and fatigue), osteoporosis and bone loss. In particular, it could be observed that patients administered by the present invention show the decreased level of alkaline phosphatase and osteocalcin, indicating the improvement in bone density, and the increased pattern of femoral bone density. In addition to this, the present invention does not induce adverse effects such as weight gain, increase of BMI (body mass index) and increase of serum cholesterol which have been reported to be observed in the conventional hormone replacement therapy.

The following specific examples are intended to be illustrative of the invention and should not be construed as limiting the scope of the invention as defined by appended claims.

EXAMPLES

Materials

Oriental pharmaceuticals of *Platycodi Radix, Cynanchum wilfordii, Phlomis umbrosa* and *Angelica gigas* were purchased in Gyeongdong Market (Seoul, Korea) and used for preparing extracts thereof.

Example 1

Preparation of Composition Containing *Platycodi Radix* Extract

Example 1-1

Preparation of Low Molecular Weight-Extract of *Platycodi Radix* Using Ultrafiltration Membrane To 50 g of dried *Platycodi Radix*, 1.5 liters of distilled water were added, followed by heating for 2 hr over room temperature for extraction, thereby obtaining aqueous extract. The extract was concentrated to final volume of 500 ml.

The extract was centrifuged at 3000 rpm for 10 min, after which for filtration the supernatant obtained was passed through ultrafiltration membrane with molecular weight cut off (MWCO) of 100,000 by means of stirred cell apparatus (purchased from Amicon, USA). The nitrogen gas pressure used was fixed at 3 atm. The extract was dried to give powder of which the amount is shown in Table 1 below.

TABLE 1

| Step | Weight (g) | Extraction Efficiency (%) |
|---|---|---|
| Raw materials | 50 | 100 |
| Extract | 14 | 28 |
| Filtration with MWCO of 100,000 | 11.5 | 23 |

Example 1-2

Preparation of Composition for Oral Administration

The composition for oral administration containing *Platycodi Radix* extract was prepared with ingredients as in Table 2.

TABLE 2

| Ingredients | Amount (Weight %) |
|---|---|
| *Platycodi Radix* extracts | 50 |
| Calcium from marine algae | 24 |
| Arginine | 16 |
| Lysine | 10 |

Example 2

Preparation of Composition for Oral Administration Containing *Cynanchum wilfordii*

Using the extract from root of *Cynanchum wilfordii*, the composition for oral administration was prepared in the same manner as in Example I-1 and I-2. The amount of the extract is shown in Table 3. The ingredients of oral composition of this invention are shown in Table 4 below.

TABLE 3

| Step | Weight (g) | Extraction Efficiency (%) |
|---|---|---|
| Raw materials | 50 | 100 |
| Extract | 15 | 30 |
| Filtration with MWCO of 100,000 | 12.1 | 24.2 |

TABLE 4

| Ingredients | Amount (Weight %) |
|---|---|
| *Cynanchum wilfordii* extract | 50 |
| Calcium from marine algae | 24 |
| Arginine | 16 |
| Lysine | 10 |

Example 3

Preparation of Composition for Oral Administration Containing *Platycodi Radix, Cynanchum wilfordii* and *Phlomis umbrosa* Extracts The extract from 50 g of *Platycodi Radix*, 25 g of root of *Cynanchum wilfordii* and 25 g of root of *Phlomis umbrosa* and the oral composition were prepared in the same manner as in Example I-1 and I-2. The amount of the extract is shown in Table 3. The ingredients of oral composition of this invention are shown in Table 4 below.

TABLE 5

| | Weight (g) | |
|---|---|---|
| Step | *Platycodi Radix* | *Cynanchum wilfordii* and *Phlomis umbrosa* |
| Raw materials | 50 | 50 |
| Extract | 14 | 36 |
| Filtration with MWCO of 100,000 | 11.5 | 30 |

TABLE 6

| Ingredients | Amount (Weight %) |
|---|---|
| *Platycodi Radix, Cynanchum wilfordii* and *Phlomis umbrosa* extracts | 50 |
| Calcium from marine algae | 24 |
| Arginine | 16 |
| Lysine | 10 |

Example 4

Efficacy Test of Composition of this Invention Using Rat

To examine the effect of composition of this invention, the compositions prepared as in Example 1, Example 2 and Example 3 were administered into rats. The concentration of estrogen in blood and the weight of sexual organ were measured in time course and anatomical and pathohistological test were performed.

Example 4-1

Oral Administration of Composition

A portion of left ovaries of 70 female rats weighted out 300 g with age of 51 weeks was removed to induce decrease in secreting amount of estrogen. Rats were sorted on their weight to distribute equally in weight into groups comprising 10 rats in a group. They were randomly distributed to 7 groups (G1, G2, G3, G4, G5, G6 and G7). 100 mg/kg of composition of Example 1-2 for G2, 1000 mg/kg of composition of Example 1-2 for G3, 100 mg/kg of composition of Example 2 for G4, 1000 mg/kg of composition of Example 2 for G5, 100 mg/kg of composition of Example 3 for G6, and 1000 mg/kg of composition of Example 3 for G7 were dissolved and suspended in distilled water acceptable to injection and administered orally in 10 mg/kg. Distilled water for injection as a control was administered to G1. For administration, rats were fixed and the composition was directly injected into their stomachs using metal sonde for oral administration injection. 10 days after the remove of ovaries, injection was done and continued for 5 weeks in once a day and 7 days per week.

Example 4-2

Measuring Estrogen Concentration in Serum

Rats fasted overnight prior to dissection were dissected 8 weeks after administration. Blood was collected from postcaval vein and stood at room temperature for 15 min for coagulation. Then, serum was separated by centrifuging at 3,000 rpm for 10 min. The separated serum was kept in −70° C. and analyzed with 1470 wizard γ counter (Perkin Elmer Life Science). Quantification of estrogen concentration in rat serum was made with EIA (enzyme immunoassay) Kit (DSL, US). The results are shown in Table 7.

TABLE 7

| | Estrogen Concentration in Serum (ng/ml) | |
|---|---|---|
| Group | Average | Standard Deviation. |
| G1 | 135.6 | 36.74 |
| G2 | 156.9 | 45.22 |
| G3 | 158.6 | 46.35 |
| G4 | 154.2 | 50.09 |
| G5 | 157.1 | 48.46 |
| G6 | 158.7 | 51.17 |
| G7 | 160.9 | 44.37 |

As shown in Table 7, the estrogen concentration in serum increased depending on injected amount in the groups administered with the composition of Example 1 containing *Platycodi Radix* extract and in the groups administered with the composition of Example 1 containing *Cynanchum wilfordii* extract. Groups administered with the composition of Example 3 containing *Platycodi Radix, Cynanchum wilfordii* and *Phlomis umbrosa* extracts showed higher estrogen concentration than groups administered with the composition of other Examples.

Accordingly, the composition containing *Platycodi Radix* extract and composition containing *Cynanchum wilfordii* extract increased estrogen concentration in serum by accelerating the estrogen secretion in female rats. In addition, the composition containing *Platycodi Radix, Cynanchum wilfordii* and *Phlomis umbrosa* extracts showed synergy effect on inducing estrogen secretion.

Example 4-3

Weighing Ovaries and Uterus

Rats in each group were dissected 8 weeks after administration and left ovaries and uterus were weighed with electronic balance (BP310S, Sartorius). The results are shown in Table 8.

TABLE 8

| | Group | | | | | | |
|---|---|---|---|---|---|---|---|
| | G1 | G2 | G3 | G4 | G5 | G6 | G7 |
| Absolute Weight of Organs (Average, g) | | | | | | | |
| Ovaries | 0.0659 | 0.0635 | 0.0695 | 0.0633 | 0.0687 | 0.0639 | 0.0699 |
| Uterus | 0.6901 | 0.6920 | 0.7989 | 0.6911 | 0.7902 | 0.6663 | 0.8181 |
| Relative Weight of Organs (Average, % body weight) | | | | | | | |
| Ovaries | 0.0228 | 0.0229 | 0.0235 | 0.0223 | 0.0230 | 0.0227 | 0.0244 |
| Uterus | 0.2425 | 0.2445 | 0.2757 | 0.2344 | 0.2703 | 0.2370 | 0.2857 |

As shown in Table 8, absolute weight of ovaries and uterus and their relative weight to body weight increased depending on injected amount in the groups administered with the composition of Example 1 containing *Platycodi Radix* extract of this invention and in the groups administered with the composition of Example 2 containing *Cynanchum wilfordii* extract of this invention.

Groups administered with the composition of Example 3 containing *Platycodi Radix, Cynanchum wilfordii* and *Phlomis umbrosa* extracts showed higher increase in absolute weight of ovaries and uterus and their relative weight to body weight.

Accordingly, it could be understood that the composition comprising *Platycodi Radix* extract and composition containing *Cynanchum wilfordii* extract propagate and regenerate tissue cells of sexual organ by inducing estrogen secretion in female rat. In addition, the composition containing *Platycodi Radix, Cynanchum wilfordii* and *Phlomis umbrosa* extracts showed synergy effect on growth of cells.

Example 4-4

Anatomical, Pathohistological Analysis

Groups administered with the composition of Example 3 and control group were dissected to analyze anatomical characteristic with naked eye. The results showed that uterus was expanded correlating to injected amount since the expansion of uterus was observed in 2 rats of control group, G1, 3 rats of G6 administered with 100 mg/kg and 5 rats of G7 administered with 1000 mg/kg. Moreover, black ovarian cyst was not observed in control group, but in 2 rats of G6 and 1 rat of G7.

The rats of above groups were fixed with 10% neutral formalin solution and trimmed. Their paraffin embedding blocks were prepared, microtomed and H&E-stained. And then, pathohistological analysis was done with optical microscope. The results are shown in Table 9.

TABLE 9

| | | No. of rat individual | | |
|---|---|---|---|---|
| Organ | Symptom | G1 | G6 | G7 |
| Uterus | Increased growth of epithelium cell in endometrium | 3 | 7 | 4 |
| | Vesiculation of grandulae uterinae in endometrium inferiores | 5 | 8 | 8 |
| | Expansion | 1 | 2 | 6 |
| | Increased growth of endometrium inferiores | 0 | 0 | 1 |
| Ovaries | Vesiculation upon vesicula expansion | 3 | 5 | 4 |
| Vagina | Increased growth of mucosal membrane epithelium cell of vagina | 5 | 6 | 7 |

As shown in Table 9, the pathohistological analysis demonstrated that the expansion of endometrial cavity and other changes related to increased growth were observed in relatively higher frequency in the groups administered with compositions of this invention, compared with the control group. Therefore, it is recognizable that the composition of this invention can induce estrogen secretion, resulting in several histological alterations associated with the growth of tissue cells from sexual organ.

CLINICAL TESTS

Test Method

This clinical test has been approved by IRB of Samsung Cheil hospital (Seoul, Korea) and complied with the Helsinki Declaration as revised in 1983.

Test groups

This study was conducted for 48 women patients with PMS (post-menopausal syndrome) who visited to the Family Medicine Clinic or Climacteric Disease Clinic Center of Samsung Cheil Hospital as a randomized and double blind comparative clinical trial. As inclusion criteria, patients were over 45 year old and diagnosed as PMS. The patients were randomly allocated to 24 of study group (treatment group) and 24 of placebo group (corn starch placebo group). Informed consents were confirmed. After written consent of the patients, their eligibilities were reexamined and serial numbers were allocated to the patients.

Dosage

The compositions for oral administration were prepared to contain 13.26% of *Phlomis umbrosa* extract, 13.26% of *Cynanchum wilfordii* extract, 14.29% of *Angelica gigas* extract, 29.52% of Seaweed calcium (from marline algae), 14.29% of L-arginine, 4.76% of L-lysine monohydrochloride, 3.81% of soy bean extract, 0.12% of dry formed Vitamin A, 0.95% of dry formed Vitamin E, 0.58% of Vitamin C (L-ascorbic acid), 0.95% of Vitamin $B_1$ (thiamine hydrochloride), 0.32% of $B_6$ (pyridoxine hydrochloride), 0.0002% of $B_{12}$ (cyanocobalamine), 0.0008% of Vitamin $D_3$ (cholecalciferol), 0.012% of biotin, 1.73% of nicotinamide, 1.18% of ferrous lactate and 0.95% of Mg stearate. It was formulated as 315 mg hard capsules. Patients were administered with the test composition as 2 capsules twice a day for 52 weeks. The extract from *Angelica gigas* was also prepared in the same manner as Example 1. The dosage for clinical test is much lower than that for animal test using rat described above.

Observation and Test Items

Age, time of menopause, pregnancy and its history and period of menopause of all patients were recorded. All patients visited the hospital at month 1, 3, 6, 9 and 12, and were examined height, weight, waist, body-mass index, blood pressure (diastolic and systolic), pulse, compliance of study material and combination medications. Hematology test items were, FSH, total cholesterol, LDL (low density lipoprotein), HDL (high density lipoprotein), triglyceride, alkaline phophatase (ALP) and osteocalcin. Bone density test was also done. Interviews about relief of climacteric symptoms for 3 months were done and recorded.

Data analysis

Patients who once had been dropped out could not be re-registered for the clinical test and early drop out patients were not replaced. Examination variables for effectiveness were treated with PP (per-protocol) analysis basically. Patients for ITT (intention-to-treat) analysis who satisfied following standard were included for PP analysis: (1) eligible to inclusion/exclusion criteria (2) compliance with the dosage of protocol over 70%; and (3) well compliance with the clinical test protocol.

Safety evaluation was performed by ITT analysis. LOCF (last-observation-carried-forward) method was used for omitted data. For ITT analysis all enrolled patients were included and drop out patients were also included. In order to evaluate effectiveness of the composition of the present invention, examination variables were measured at week 0, week 4, week 12, week 24, week 36 and week 52 and differences from baseline were analyzed by Mann-Whitney test and Fisher's exact test. In two-tailed test the analysis were performed with 5% significance. SPSS for Windows 10.0 (SPSS Inc., Chicago, Ill., USA) was used for the statistical analysis.

Results

To evaluate effectiveness and safety of the composition of the present invention, the total 48 patients enrolled to the test at Samsung Cheil hospital. The safety was evaluated for the 48 patients. The effectiveness was evaluated for 42 patients who completed the whole test procedure complied to protocol except for 5 self denied patients and 1 patient having shown adverse event.

General Characteristics of the Test Group at Baseline

Total enrolled patients were 48 and 6 patients were dropped out of the test. In result, 23 patients were in the placebo group and 19 patients were in the treatment group. Average age of the patients was 54 ranging from 46 to 66. Age distribution of the patients is noted in the Table 10 and 6 patients (14.3%) were over 61-year old (Table 10).

TABLE 10

| Demographic characteristics | | |
|---|---|---|
| | | Number of patients |
| Total patients | | 42 (100%) |
| Age | 46-50 | 13 (31.0%) |
| | 51-60 | 23 (54.8%) |
| | 61-66 | 6 (14.3%) |

At baseline of the test there were no significant differences in physical profiles, baseline hormone concentrations and serum lipid profiles between the treatment group and the placebo group but the mean ossification rate was higher in the treatment group (Table 11).

TABLE 11

| Basic characteristics of patients before clinical test | | | |
|---|---|---|---|
| | Case average | Control average | Total average |
| L2 BMD(g/cm$^2$) | 0.943 ± 0.14 | 0.834 ± 0.15 | 0.883 ± 0.15 |
| L3 BMD(g/cm$^2$) | 1.003 ± 0.14 | 0.897 ± 0.16 | 0.945 ± 0.16 |
| L4 BMD(g/cm$^2$) | 1.044 ± 0.15 | 0.922 ± 0.17 | 0.977 ± 0.17 |
| L2-4 BMD(g/cm$^2$) | 0.996 ± 0.14 | 0.888 ± 0.16 | 0.936 ± 0.16 |
| Neck BMD (g/cm$^2$) | 0.746 ± 0.10 | 0.743 ± 0.10 | 0.744 ± 0.10 |
| Troch anter BMD (g/cm$^2$) | 0.639 ± 0.09 | 0.617 ± 0.10 | 0.627 ± 0.10 |
| Inter trochanter BMD (g/cm$^2$) | 1.047 ± 0.15 | 1.021 ± 0.12 | 1.033 ± 0.13 |
| Total neck BMD (g/cm$^2$) | 0.866 ± 0.12 | 0.856 ± 0.09 | 0.861 ± 0.10 |
| Ward BMD (g/cm$^2$) | 0.607 ± 0.13 | 0.565 ± 0.13 | 0.585 ± 0.13 |
| FSH (mIu/ml) | 52.400 ± 32.80 | 56.037 ± 32.74 | 54.489 ± 32.46 |
| Osteocalcin(ng/ml) | 6.020 ± 2.74 | 6.241 ± 3.04 | 6.147 ± 2.89 |
| βcross lab(ng/ml) | 0.470 ± 0.21 | 0.591 ± 0.30 | 0.540 ± 0.27 |
| Alkaline Phosphatase(IU/L) | 73.350 ± 21.02 | 74.407 ± 27.33 | 73.957 ± 24.59 |
| hGh(ng/ml) | 0.250 ± 0.21 | 0.573 ± 0.71 | 0.461 ± 0.60 |
| IGF-1(ng/ml) | 265.556 ± 76.82 | 271.438 ± 48.87 | 234.760 ± 63.37 |
| Fasting Glucose(mg/dl) | 99.400 ± 22.58 | 103.296 ± 11.30 | 101.638 ± 16.93 |
| Cholesterol(mg/dl) | 182.750 ± 36.19 | 203.000 ± 38.68 | 194.383 ± 38.59 |
| HDL (mg/dl) | 46.850 ± 8.44 | 46.815 ± 13.13 | 46.830 ± 11.26 |
| LDL (mg/dl) | 112.080 ± 33.75 | 133.156 ± 33.02 | 124.187 ± 34.61 |
| Triglyceride(mg/dl) | 119.100 ± 54.72 | 115.148 ± 37.63 | 116.830 ± 45.18 |
| Weight(kg) | 57.332 ± 5.84 | 57.243 ± 6.12 | 57.279 ± 5.94 |
| Height(cm) | 157.300 ± 3.74 | 153.852 ± 5.41 | 155.319 ± 5.03 |
| WtoH | 0.808 ± 0.04 | 0.834 ± 0.04 | 0.824 ± 0.04 |
| BMI(kg/m$^2$) | 23.133 ± 1.79 | 24.123 ± 2.12 | 23.714 ± 2.03 |

TABLE 11-continued

Basic characteristics of patients before clinical test

|  | Case average | Control average | Total average |
|---|---|---|---|
| Systolic Pressure(mmHg) | 117.000 ± 13.89 | 113.038 ± 17.67 | 114.711 ± 16.13 |
| Diastolic Pressure(mmHg) | 76.474 ± 8.32 | 73.846 ± 10.75 | 74.956 ± 9.78 | p > 0.05, Mann-Whiteney test
BMD: Bone Mineral Density
FSH; Follicuar Stimulating Hormone,
hGH; human Growth Hormone,
HDL; High Density Lipoprotein,
LDL; Low Density Lipoprotein,
WtoH; Waist to Hip Ratio,
BMI; Body Mass Index Result of Primary Endpoint Evaluation (Interview on the Improvement of the PMS Symptoms)

Change of Climacteric Symptoms 3 Months After the Commencement of the Test

In examination of the changes of PMS symptoms after 3 months the treatment group showed better improvement of various PMS symptoms than the placebo group with statistic significance. The possibility of the symptom improvements of treated patients is about five times more than the placebo group. In detail, 9 cases of dyspareunia, 5 of hot flush, 1 of sleep disorder, 2 of mental awareness problem, 1 of joint pain, 1 of musculoskeletal disease, 2 of dyspepsia, 1 of urinary incontinence and 1 of fatigue in 14 patients were relieved. The changes are summarized in Table 12.

TABLE 12

Change of climacteric symptoms 3 months after test commence

|  |  | change of climacteric symptoms | | |
|---|---|---|---|---|
|  |  | No improvement | Improvement | Total |
| Placebo group | case(n) | 18 | 5 | 23 |
|  | (%) | 78.3% | 21.7% | 100.0% |
| Treatment group | case(n) | 10 | 14 | 24 |
|  | (%) | 41.7% | 58.3% | 100.0% |
| Total | case(n) | 28 | 19 | 47 |
|  | (%) | 59.6% | 40.4% | 100.0% |

OR = 5, 04 (95% C.I.: 1.4-18.1)
Fisher's Exact Test

Changes in the Patients with Climacteric Symptoms at Baseline

Patients of the treatment group showed more improvement in the symptoms compared to the placebo group. The changes of the symptoms are summarized in Table 13.

TABLE 13

Change in the patients with climacteric symptoms at baseline

|  |  | change of climacteric symptoms | | |
|---|---|---|---|---|
|  |  | No improvement | Improvement | Total |
| Placebo group | case(n) | 5 | 1 | 6 |
|  | (%) | 83.3% | 16.7% | 100.0% |
| Treatment group | case(n) | 3 | 4 | 7 |
|  | (%) | 42.9% | 51.7% | 100.0% |
| Total | case(n) | 8 | 5 | 13 |
|  | (%) | 61.5% | 38.5% | 100.0% |

OR = 6.67 (95% C.I.: 0.49-91.3) Fisher's Exact Test

Result of Secondary Endpoint Evaluation (Evaluation of Effectiveness at 12 Months of Administration)

In terms of the absolute and comparative changes of several variables between baseline and month 12, there was no significant statistic difference between the two groups (treatment group and placebo group) on weight, BMI, blood pressure, FSH, total cholesterol, LDL, HDL and spinal bone density. But femoral bone density was increased in the treatment group with statistical significance (p<0.05). Serum ALP (alkaline phosphatase) was decreased in the treatment group and the significance was borderline level (p=0.08). Serum osteocalcin concentration was decreased in the treatment group, while it was increased in the placebo group (p<0.05). Serum TG concentration was decreased in the treatment group and the significance was borderline level (p=0.66)

Change of Femoral Bone Density

The change of femoral bone density is indicated Table 14. The density change showed increase of 0.017±0.03 (2.24%) (from 0.746±0.10 g/cm$^2$ at baseline to 0.763±0.13 g/cm$^2$ at month 12) in the treatment group but showed decrease of 0.01±0.04 g/cm$^2$ (1.14%) (from 0.743±0.10 g/cm$^2$ at baseline to 0.733±0.13 g/cm$^2$ at month 12) in the placebo group. The treatment showed statistically significant increase in femoral bone density (p<0.05). Moreover, considering CV value of hologic BMD measurement was changed to 1-2%, the proportion of patients who showed increase of bone density by more than 0% or by more than 5% was higher in the treatment group and it was statistically significant. The proportions of patients showing increased pattern in femoral bone density are noted in Tables 15 and 16.

TABLE 14

| Change of femoral bone density (g/cm$^2$) | | |
|---|---|---|
|  | Treatment group | Placebo group |
| Baseline | 0.746 ± 0.10 | 0.743 ± 0.10 |
| Month 12 | 0.763 ± 0.13 | 0.733 ± 0.14 |

P < 0.05, Mann-Whitney test

TABLE 15

Proportion of patients showing increasing pattern by more than 0% in femoral bone density

|  |  |  | Case Control | | |
|---|---|---|---|---|---|
|  |  |  | Placebo group | Treatment group | Total |
| Femoral bone density | Decrease Or Unchanged | Case (%) | 11 52.4% | 8 42.1% | 19 100.0% |
|  | Increase | Case (%) | 10 47.6% | 11 57.9% | 21 100.0% |
| Total |  | Case (%) | 21 1100.0% | 19 100.0% | 40 100.0% |

Fisher's Exact Test OR = 1.53
95% C.I.: (0.43-5.28)

TABLE 16

Proportion of patients showing increasing pattern by more than 5% in femoral bone density

|  |  |  | Case Control | | |
|---|---|---|---|---|---|
|  |  |  | Placebo group | Treatment group | Total |
| Femoral bone density | Decrease Or Unchanged | Case (%) | 18 85.7% | 15 78.9% | 33 82.5% |
|  | Increase | Case (%) | 3 14.3% | 4 21.1% | 7 17.5% |
| Total |  | Case (%) | 21 100.0% | 19 100.0% | 40 100.0% |

Fisher's Exact Test OR = 1.60
95% C.I. (0.30-8.30)

Changes of Serum ALP and Osteocalcin

As shown in Table 17, there was no significant difference of serum ALP concentrations between the two groups at baseline. However, at the end of the test, the ALP (alkaline phosphatase) concentration of the treatment group was 60.42±14.87 IU/L and that of the placebo group was 71.00±32.54 IU/L. The mean value of the treatment group was significantly decreased and their statistical significance was borderline level (Mann-Whintey Test p=0.08). In the proportion of patients showing over 5% of decrease in ALP at 12 months of the administration, the treatment group was 78.9% and the placebo group was 54.5% (Table 18). Serum osteocalin concentration was decreased in the treatment group (6.02±2.74 ng/ml at baseline and 5.66±3.01 ng/ml at month 12) but was increased in the placebo group (6.24±3.04 ng/ml at baseline and mean 5.66±3.01 ng/ml at month 12) at month 12. The changes were different significantly (Mann-Whitney Test p<0.05).

TABLE 17

Change of serum ALP level (IU/L)

|  | Treatment group | Placebo group |
|---|---|---|
| Baseline | 73.35 ± 21.02 | 74.23 ± 27.17 |
| Month 12 | 60.42 ± 14.87 | 71.00 ± 32.54 |

P < 0.05, Mann-Whitney test

TABLE 18

Proportions of patients showing the decrease of serum ALP

|  |  |  | Case Control | | |
|---|---|---|---|---|---|
|  |  |  | Placebo group | Treatment group | Total |
| Change of Serum ALP | Increase Or Unchanged | Case (%) | 10 45.5% | 4 21.1% | 14 34.1% |
|  | Decrease | Case (%) | 12 54.5% | 15 78.9% | 27 65.9% |
| Total |  | Case (%) | 22 100.0% | 19 100.0% | 41 100.0% |

Fisher's Exact Test OR = 3.13
95% C.I. (0.78-12.50)

Change of Weight and BMI

Figure 1:
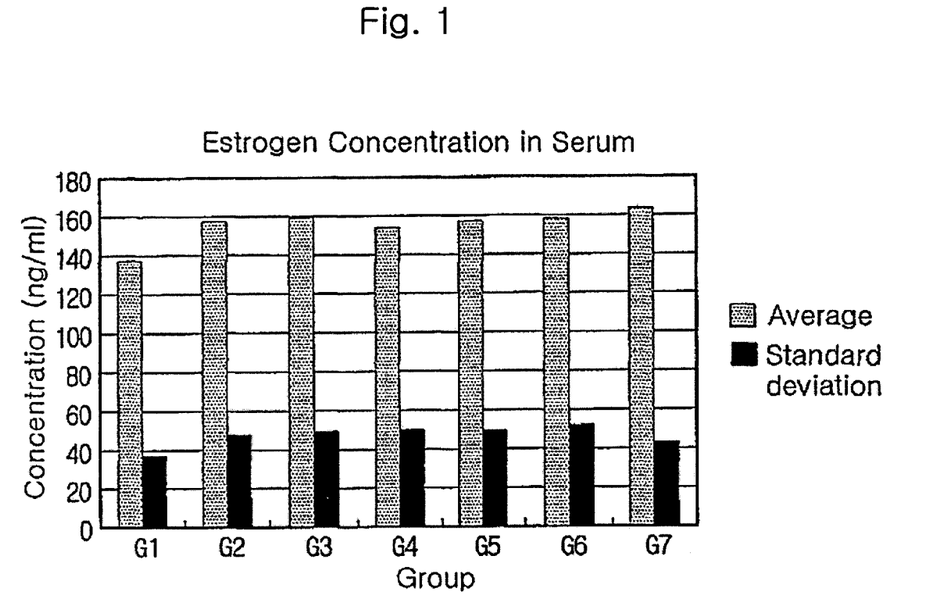
FIG. 1 is a graph representing the average estrogen concentration in serum of rats administered with the composition of this invention for each group.
Figure 2A:
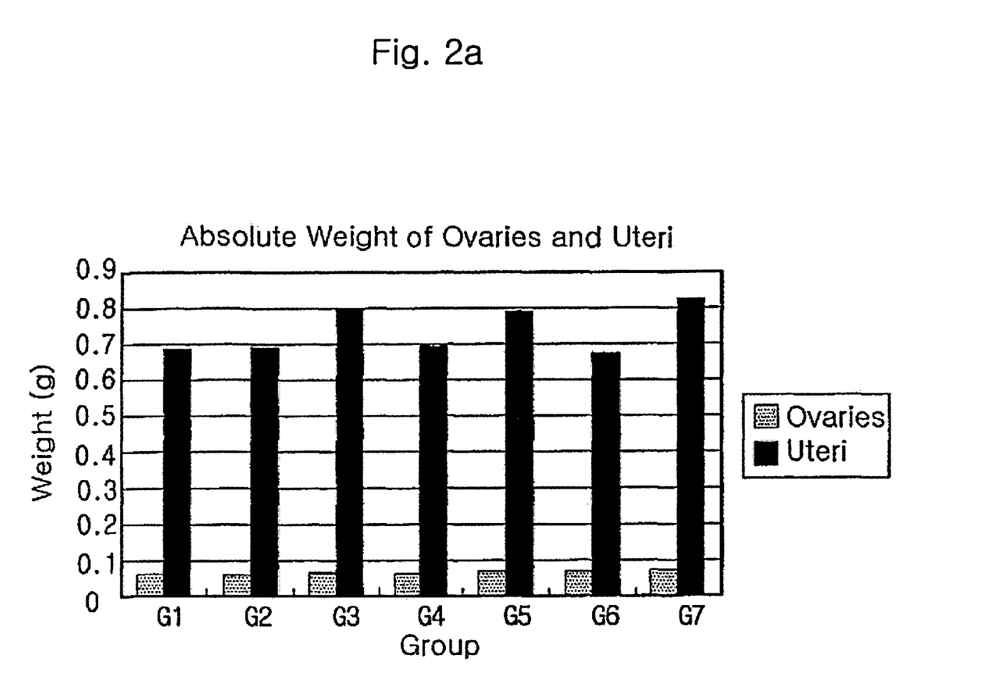
FIG. 2*a* is a graph representing the average weight of ovaries and uterus of rats administered with the composition of this invention for each group.
Figure 2B:
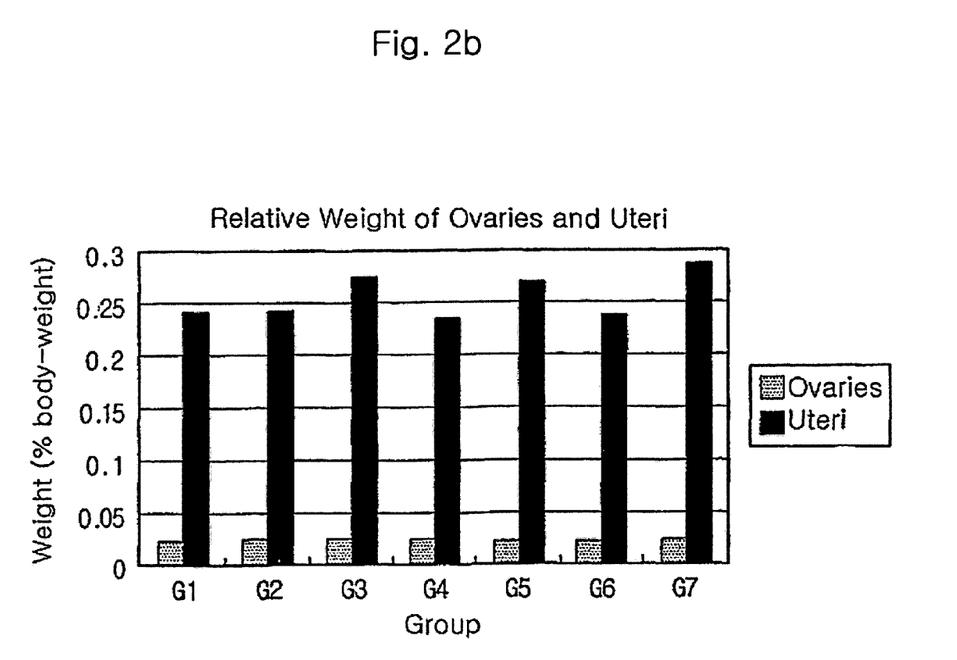
FIG. 2*b* is a graph representing the average relative weight of ovaries and uterus of rats administered with the composition of this invention for each group.
Figure 3:
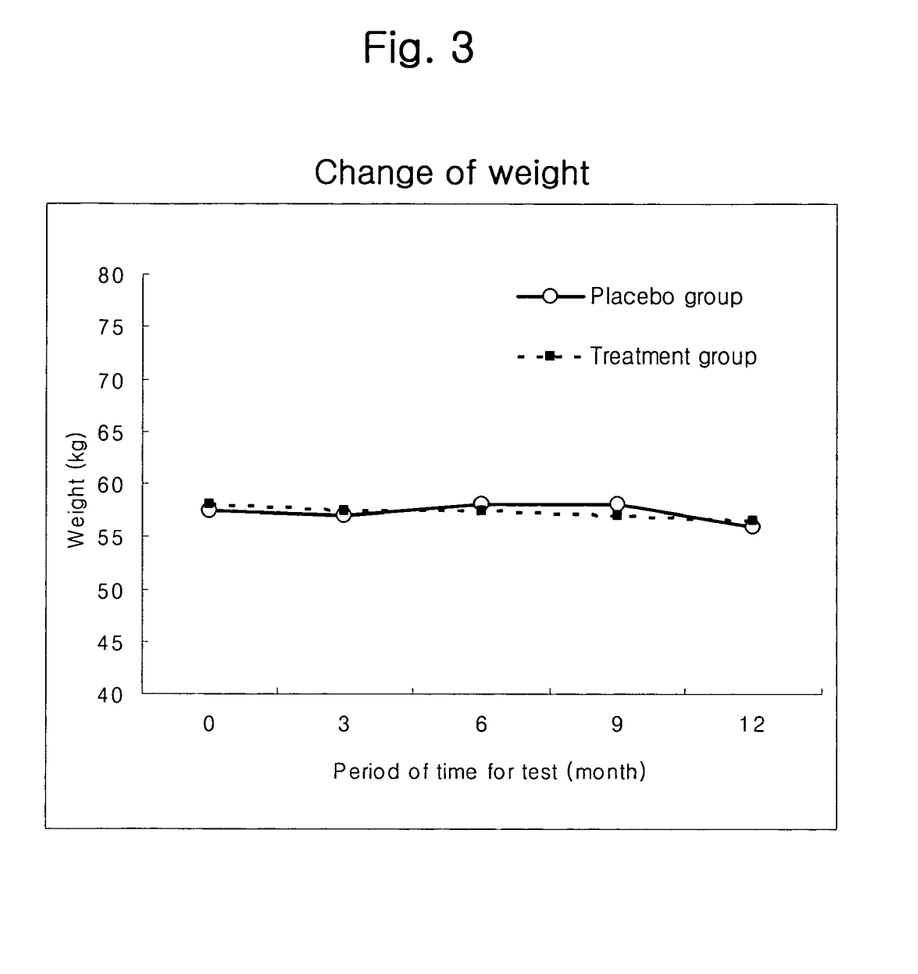
FIG. 3 is a graph representing the change of weight of patients in the treatment group and placebo group over clinical test.

At the end of the clinical test, the weight and BMI of patients remained unchanged in the treatment group while common HRT often induce weight gains. The change of weight after the test is noted in FIG. 3.

Serum Lipid Profiles

Figure 4A:
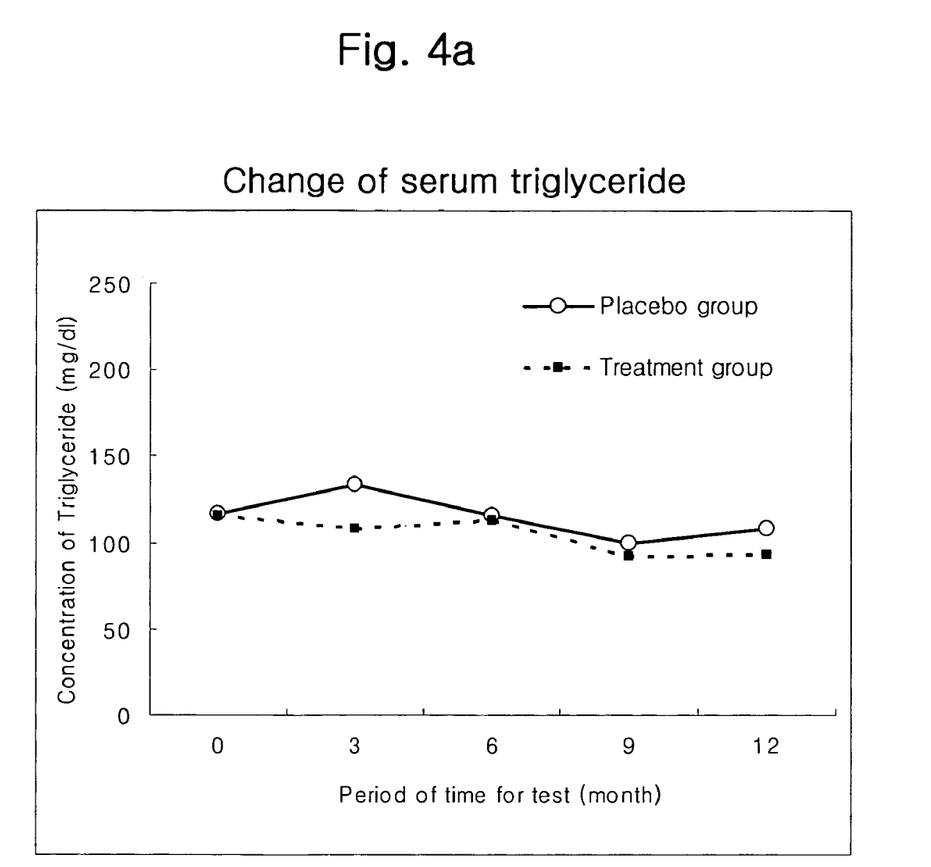
FIG. 4*a* is a graph representing the change of TG (triglyceride) level of patients in the treatment group and placebo group over clinical test.
Figure 4B:
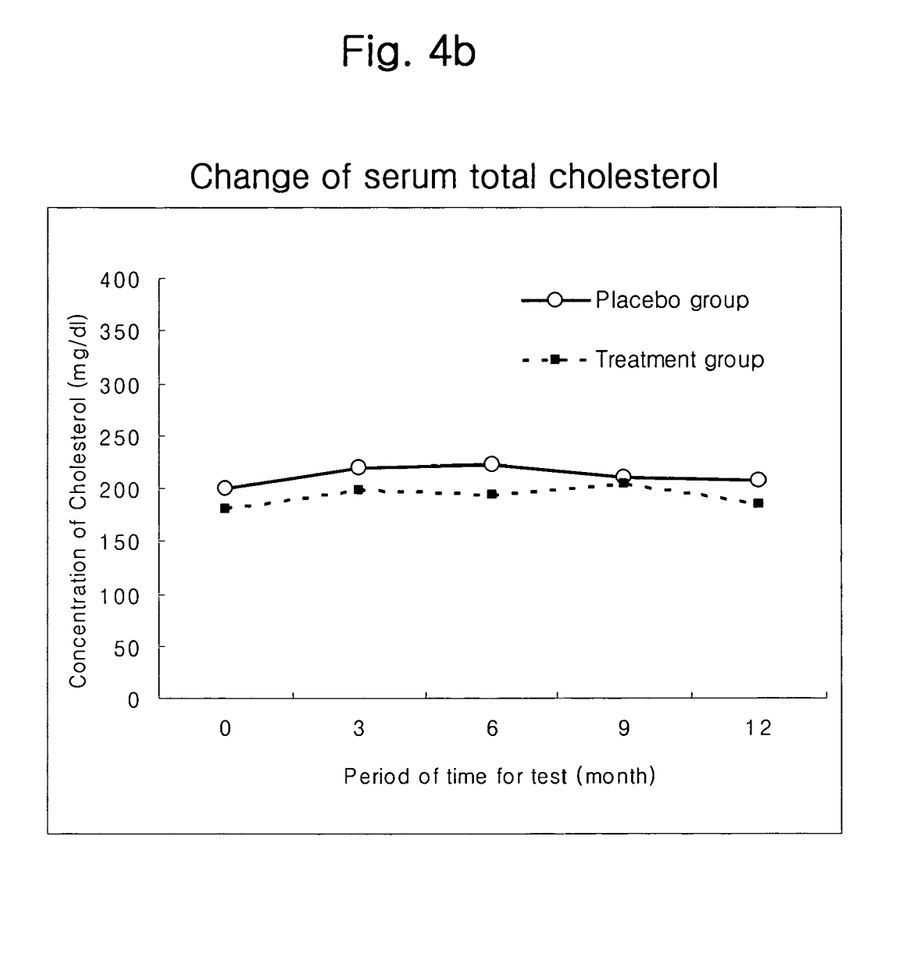
FIG. 4*b* is a graph representing the change of serum cholesterol level of patients in the treatment group and placebo group over clinical test.

The changes of serum TG and total cholesterol concentrations are depicted in FIGS. 4a and 4b. In serum TG, there was no significant change in the placebo group but the treatment group showed significant decrease from 119.1±54.72 mg/dl at baseline to 92.16±49.94 mg/dl at month 12. The significance of change in the treatment group was at borderline concentration (Mann-Whitney Test, p=0.66). Serum cholesterol did not show significant changes in both two groups and there was not increase of serum cholesterol in the treatment group. And there were observed little changes in LDL and HDL concentrations.

As described previously, the present invention provides a composition, a pharmaceutical composition and a food composition capable of replacing estrogen, and a method for treating or preventing a disease, disorder or symptom associated with menopause. The present invention uses a composition comprising as an active ingredient one or more selected from the group consisting of an extract from *Platycodon grandiflorum*, an extract from *Cynanchum wilfordii*, an extract from *Phlomis umbrosa* and an extract from *Angelica gigas*. The composition of this invention comprised of the extracts of natural source shows little or no adverse effects such as cancer occurrence compared with estrogen-replacing agent used for conventional hormone replacement therapy. Moreover, the composition of this invention has little impurities and high amount of active ingredients.

Having described specific examples of the present invention, it is to be understood that such examples are only preferred embodiments and should not be construed as limiting the scope of the invention. Therefore, the substantive scope of the invention may be determined by appended claims and their equivalents.

What is claimed is:

1. A method for alleviating menopausal symptoms of dyspareunia, hot flush, sleep disorder, dyspepsia, or urinary incontinence, which comprises administering to menopausal women suffering from menopausal symptoms of dyspareunia, hot flush, sleep disorder, dyspepsia, or urinary incontinence, a therapeutically effective amount of a composition comprising as an active ingredient an extract from a root of *Cynanchum wilfordii*, an extract from a root of *Phlomis umbrosa* or its combination.

2. The method according to claim 1, wherein the composition further comprises as the active ingredient an extract from *Platycodon grandiflorum*.

3. The method according to claim 2, wherein the composition comprises as the active ingredient the extract from *Platycodon grandiflorum*, the extract from the root of *Cynanchum wilfordii* and the extract from the root of *Phlomis umbrosa*.

4. The method according to claim 1, wherein the composition is a pharmaceutical, health supplement or food composition.

5. The method according to claim 1, wherein the extract is an active fraction prepared in a process which comprises contacting *Platycodon grandiflorum*, *Cynanchum wilfordii* or *Phlomis umbrosa* with a hot water for obtaining an extract; and filtering the extract through an ultrafiltration membrane with a molecular weight cut off of 50,000-100,000.

6. The method according to claim 1, wherein the composition further comprises one or more ingredients selected from the group consisting of calcium, arginine, lysine and vitamins.

* * * * *